(12) United States Patent
Tucker

(10) Patent No.: US 11,234,631 B2
(45) Date of Patent: *Feb. 1, 2022

(54) METHOD AND SYSTEM FOR CONTROLLING NEURAL ACTIVITY IN THE BRAIN

(71) Applicant: Magstim Group, Incorporated, Eden Prairie, MN (US)

(72) Inventor: Don M. Tucker, Eugene, OR (US)

(73) Assignee: Magstim Group, Incorporated, Eden Prairie, MN (US)

( * ) Notice: Subject to any disclaimer, the term of this patent is extended or adjusted under 35 U.S.C. 154(b) by 455 days.

This patent is subject to a terminal disclaimer.

(21) Appl. No.: 16/033,700

(22) Filed: Jul. 12, 2018

(65) Prior Publication Data

US 2018/0318584 A1 Nov. 8, 2018

Related U.S. Application Data

(60) Continuation of application No. 15/437,765, filed on Feb. 21, 2017, now Pat. No. 10,065,034, which is a continuation of application No. 15/058,475, filed on Mar. 2, 2016, now abandoned, which is a continuation of application No. 13/863,724, filed on
(Continued)

(51) Int. Cl.
| | |
|---|---|
| *A61B 5/369* | (2021.01) |
| *A61B 5/055* | (2006.01) |
| *G01R 33/32* | (2006.01) |
| *G01R 33/48* | (2006.01) |
| *A61N 1/36* | (2006.01) |
| *A61B 5/291* | (2021.01) |
| *A61B 5/375* | (2021.01) |

(Continued)

(52) U.S. Cl.
CPC .............. *A61B 5/369* (2021.01); *A61B 5/055* (2013.01); *A61B 5/0536* (2013.01); *A61B 5/291* (2021.01); *A61B 5/375* (2021.01); *A61N 1/0456* (2013.01); *A61N 1/36031* (2017.08); *A61N 1/36034* (2017.08); *G01R 33/323* (2013.01); *G01R 33/4808* (2013.01); *A61B 2576/026* (2013.01)

(58) Field of Classification Search
USPC ......................................... 600/383, 544, 411
See application file for complete search history.

(56) References Cited

U.S. PATENT DOCUMENTS

| 2005/0167588 A1* | 8/2005 | Donnangelo | ........ A61B 5/0536 250/307 |
| 2007/0208212 A1* | 9/2007 | DiLorenzo | ........... A61B 5/1101 600/26 |

(Continued)

OTHER PUBLICATIONS

Sadleir, R. J., S. C. Grant, and E. J. Woo. "Can high-field MREIT be used to directly detect neural activity? Theoretical considerations." Neuroimage 52.1 (2010): 205-216 (Sadleir) (Year: 2010).*

(Continued)

*Primary Examiner* — Christian Jang
*Assistant Examiner* — Mitchell E Alter
(74) *Attorney, Agent, or Firm* — Kilpatrick Townsend & Stockton LLP

(57) ABSTRACT

A method and system for controlling neural activity in the brain, including performing a source localization procedure and a neurostimulation procedure, and using the former as a monitor to provide for feedback control of the latter.

5 Claims, 3 Drawing Sheets

Related U.S. Application Data

Apr. 16, 2013, now Pat. No. 9,326,699, which is a division of application No. 12/928,914, filed on Dec. 21, 2010, now abandoned.

(51) Int. Cl.
   *A61B 5/0536* (2021.01)
   *A61N 1/04* (2006.01)

(56) References Cited

U.S. PATENT DOCUMENTS

| | | | | |
|---|---|---|---|---|
| 2009/0326608 | A1* | 12/2009 | Huynh | A61N 1/36185 |
| | | | | 607/59 |
| 2010/0010369 | A1* | 1/2010 | Pomfrett | A61B 5/0042 |
| | | | | 600/554 |
| 2012/0109004 | A1* | 5/2012 | Cadwell | A61B 34/10 |
| | | | | 600/554 |

OTHER PUBLICATIONS

Woo, Eung Je, and Jin Keun Seo. "Magnetic resonance electrical impedance tomography (MREIT) for high-resolution conductivity imaging." Physiological measurement 29.10 (2008): R1 (Woo). (Year: 2008).*

"Instrumentation and Signal Processing for Low-frequency Bounded-EIT Studies of the Human Head" Poolman, P, et al., IEEE International Instrumentation and Measurement Technology Conference, Victoria, Vancouver Island, Canada, May 12-15, 2008 (Poolman) (Year: 2008).*

* cited by examiner

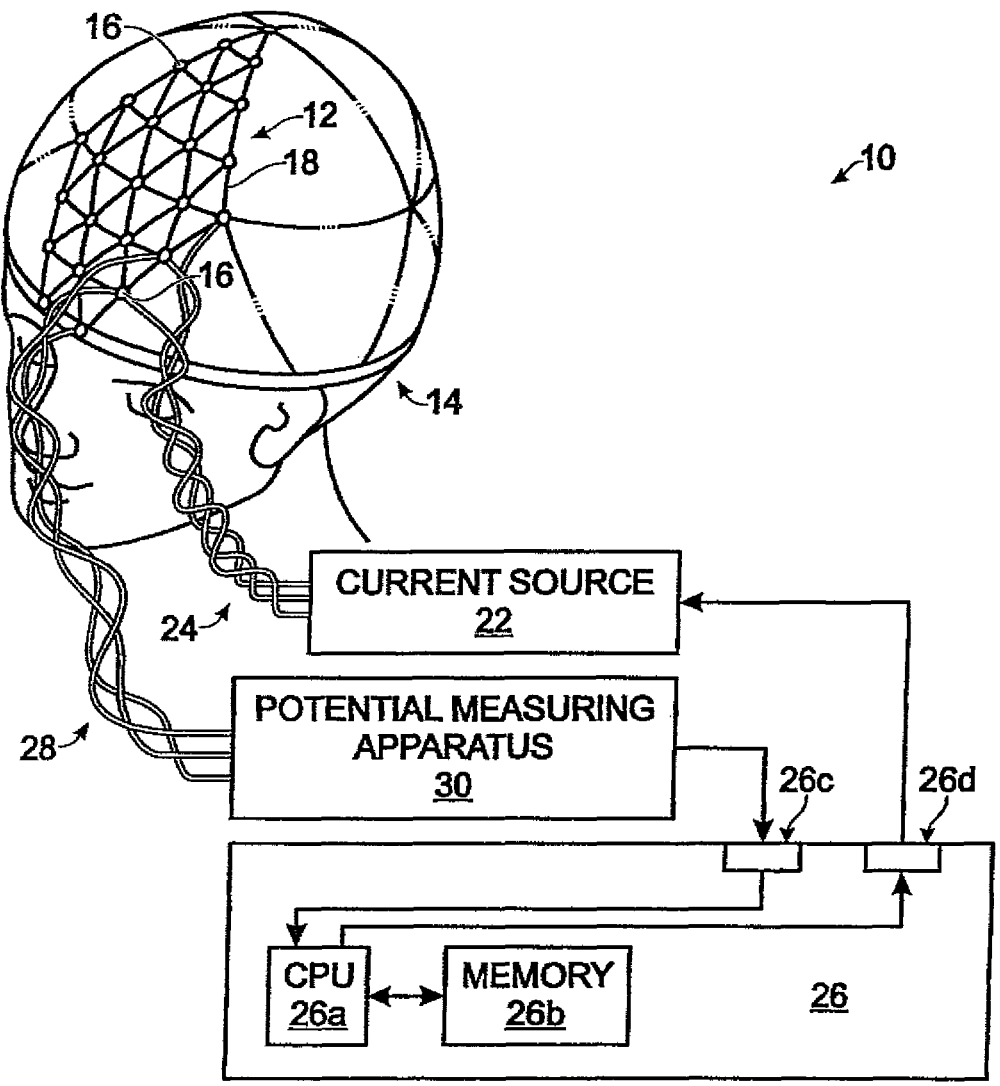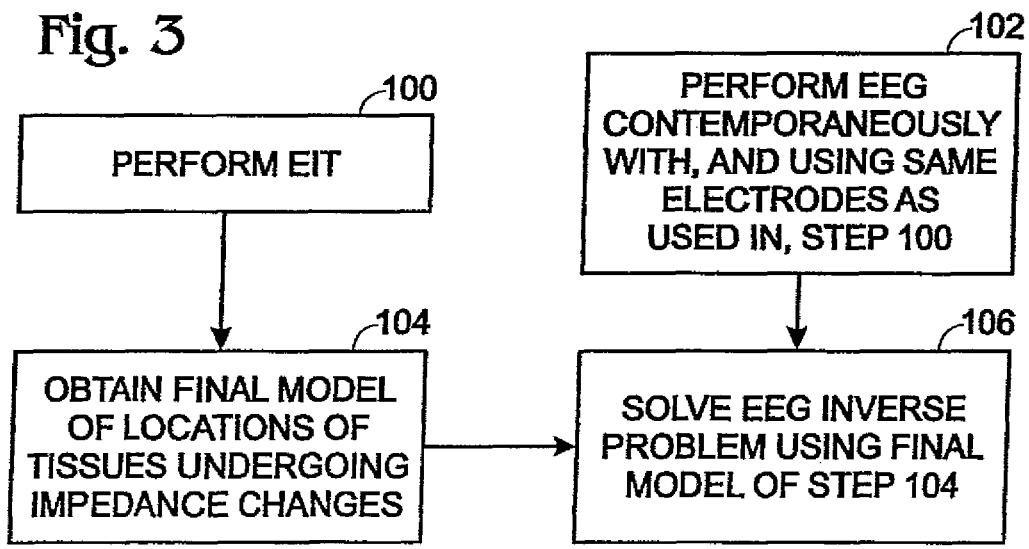

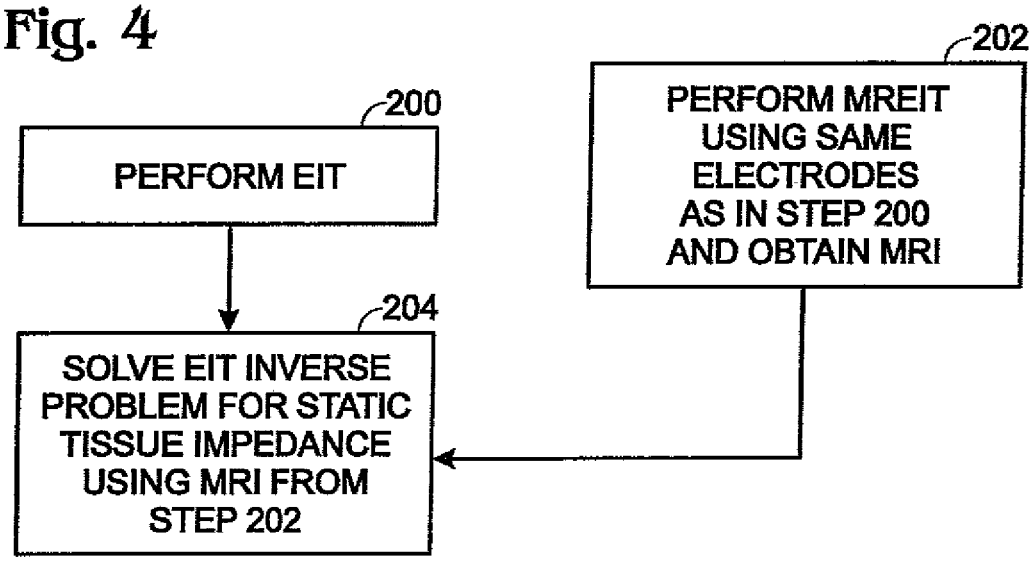
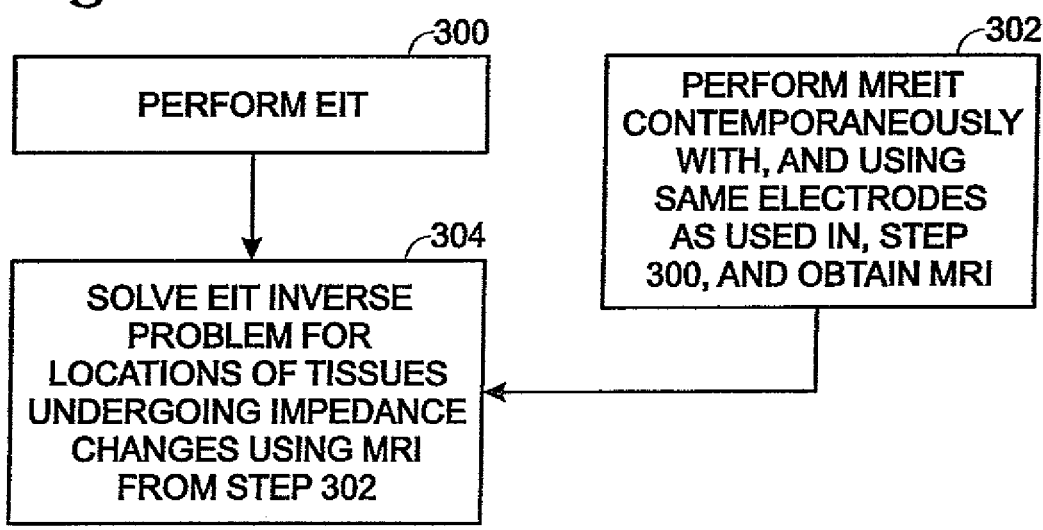

METHOD AND SYSTEM FOR CONTROLLING NEURAL ACTIVITY IN THE BRAIN

RELATED APPLICATIONS

This is a continuation of U.S. Ser. No. 15/437,765, filed Feb. 21, 2017, which is a continuation of U.S. Ser. No. 15/058,475, filed Mar. 2, 2016, now abandoned, which is incorporated by reference herein in its entirety, which is a continuation of U.S. Ser. No. 13/863,724, filed Apr. 16, 2013, now U.S. Pat. No. 9,326,699, which is a divisional of U.S. Ser. No. 12/928,914, filed Dec. 21, 2010, now abandoned.

FIELD OF INVENTION

The present invention relates to electrical impedance tomography, magnetic resonance electrical impedance tomography, electroencephalography, and neurostimulation.

BACKGROUND OF INVENTION

Electrical impedance tomography (hereinafter AEIT@) is a known technique for non-invasive spatial mapping of the electrical resistance (referred to by use of the more general term Aimpedance@) of internal body tissues. The tissue impedance varies with tissue type and health, and it also varies temporally, on the order of 10 milliseconds (ms) or less, as a result of electrical activity occurring within the body tissues. A particularly important source of electrical activity in the body is the brain, and the present invention is particularly focused on EIT used to map the impedance of tissues associated with the brain, e.g., cortex (white and gray matter), cerebrospinal fluid, skull, and scalp.

In ordinary EIT used as a tool for probing the brain, an array of electrodes is applied to the head surface. Typically, the array consists of 256 electrodes, and it is desirable to provide as many electrodes as is practical, i.e., it is desirable to have a Adense@ array.

Each electrode is used to Ainject@ an electrical current into the head, i.e., into the tissues the impedances of which it is desired to ascertain, and the remaining electrodes are used to measure the spatial distribution of the resulting electrical potentials that arise at the surface of the head.

Determining the internal tissue impedances responsible for the measured potentials in view of the known injected currents is an example of what is well known in the art as an Ainverse problem.@ An inverse problem is generally to deduce unknown structure in view of the structure=s known responses to known stimuli. To Asolve@ an inverse problem is generally to hypothesize a mathematical model for the unknown structure, test the model by applying the known stimuli mathematically to determine whether its output agrees with those actually measured, assess the error, adjust the model to try to reduce the error, and iterate these steps until a convergence is obtained that represents an optimum solution.

Inverse problems are generally Aill-posed,@ or ambiguous, so that it is generally understood to be important to Aconstrain@ the iterative solution process by known relevant facts. One way of constraining the solutions is to provide for greater resolution in the data, which is the reason for preferring the dense array. Also, typically, for solving inverse problems associated with probing internal anatomy such as the brain, anatomical constraints are utilized, such as may be obtained by magnetic resonance imaging (MRI).

EIT is used herein as a generic term that includes ordinary EIT as well as magnetic resonance EIT, or AMREIT.@ MREIT is also a known technique in which a magnetic resonance (AMR@) image is obtained of the injected currents, from which the current density can be determined, which in turn allows for determining impedance.

MREIT does not require solving an inverse problem, and its spatial resolution is superior to that of EIT. On the other hand, EIT does not require use of an expensive MR imaging machine.

EIT has also been considered as a tool for imaging dynamic neural functions in the brain. When neurons Afire@ (i.e., depolarize), they transfer ions into the extracellular space, decreasing their soma size and cross-section for conducting current, decreasing their electrical impedance. Conversely, when the neurons polarize they absorb ions from the extracellular space, increasing their soma size and cross-section for conducting current, increasing their electrical impedance. Once the ordinary EIT inverse problem has been solved, i.e., once a satisfactory model of the static impedances has been identified, the same model can in principle be used to very quickly localize changes in impedance associated with neural function. Unfortunately, the impedance changes are too small to be reliably discerned, and EIT is not considered to be a useful imaging modality.

Electroencephalography (AEEG@) measures the electrical activity of the brain. When neural activity (the ongoing synaptic effects) changes the polarization of the soma of pyramidal neurons of the cortex (which are aligned and therefore create far fields), there is a change in the polarity between the soma at the apical dendrites (toward the surface of the cortex). For example, greater negativity at the soma leads to relative positivity at the apical dendrites, creating a dipole and thus a dipolar field. These dipoles are referred to as Asources,@ and EEG is used to localize the sources. In EEG, an array of electrodes is applied to the head surface, and each electrode is used to measure electrical potentials that arise at the surface of the head in response to source activity.

EEG source localization also presents an inverse problem, so again, it is particularly desirable to provide a dense array for EEG (dEEG). The inverse problem is particularly to deduce the locations and relatives strengths of the sources as would be needed to produce the measured distribution of surface potentials, and it is solved in the same general manner indicated above.

While EEG is a standard brain imaging tool, any tool that requires solving an inverse problem will have limited capability. Recognizing this, the present inventor developed the method described in U.S. Patent Publication No. 20030093005, which combines images produced by EEG and MRI to enhance resolution.

SUMMARY OF INVENTION

Methods for use of EIT are disclosed herein. The generic method has four aspects.

All four aspects include performing an EIT procedure, which is defined to include distributing a plurality of electrodes on a subject=s head such that each electrode makes electrical contact with the head surface at a respective location that is spaced apart from the location associated with each other electrode, and performing an EIT current injecting step by injecting a first set of currents into the head, each of the currents of the first set being injected by a corresponding two or more of the electrodes and having a sufficiently small magnitude so as not to provoke a substantial brain response, either alone or in combination with other currents of the first set, and, during a time when the first set of electrodes is injecting one or more of the currents of the first set, utilizing a plurality of the remaining electrodes to measure respective first electrical potentials arising in response.

At least one of an EEG procedure and an MREIT procedure, using the same electrodes as used for performing the EIT procedure, is performed.

The EEG procedure is defined to include measuring, at the aforementioned remaining electrodes, respective second electrical potentials resulting from the electrical activity of one or more sources in the brain during the same time that the at least two or more electrodes are injecting a current. A final solution to an EIT inverse problem for the distribution of static tissue impedances in the head posed by the first injected currents and the first electrical potentials is obtained. Also obtained are one or more iterative solutions to an EEG inverse problem for localizing the sources posed by the second electrical potentials. The EIT final solution is used as a constraint on one or more of the EEG solutions.

The MREIT procedure is defined to include performing an MREIT current injecting step that is the same as the EIT current injecting step. Also, a magnetic resonance image of the currents injected in the MREIT current injecting step is obtained, and the method includes either or both the following steps: (c) obtaining one or more iterative EIT solutions to an inverse problem for the distribution of static tissue impedances in the head posed by the first injected currents and the first electrical potentials, or (d) obtaining one or more iterative EIT solutions to an inverse problem for localizing head tissues undergoing changes in impedance which is also posed by the first injected currents and the first electrical potentials. The solutions referred to as (c) and (d) are constrained by the magnetic resonance image.

Preferably, the constraints provided by the magnetic resonance image, if the MREIT procedure is performed, and by the EIT, if the EEG is performed and the EIT is used as a constraint on solutions to the EEG inverse problem, are computed or otherwise provided in the form of Bayesian conditional probabilities.

In a second embodiment of the invention, any one or any combination of the aforementioned methods is used as a monitor to provide feedback for adjusting injected currents provided for the purpose of neurostimulation. A particularly advantageous use of the second embodiment is to adjust the phase of neural activity by adjusting the timing of the stimulating currents in response to the feedback.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

BRIEF DESCRIPTION OF DRAWINGS

FIG. 1 is a schematic/block diagram of a standard system for performing EIT.

FIG. 3 is a flow diagram of a methodology according to a second aspect of the present invention, combining EIT used as a dynamic neural function imaging modality with EEG.

FIG. 4 is a flow diagram of a methodology according to a third aspect of the present invention, combining EIT used as a static tissue impedance modeling modality with MREIT.

FIG. 5 is a flow diagram of a methodology according to a fourth aspect of the present invention, combining EIT used as a dynamic neural function imaging modality with MREIT.

DESCRIPTION OF PREFERRED EMBODIMENTS

First Embodiment

Figure 2:
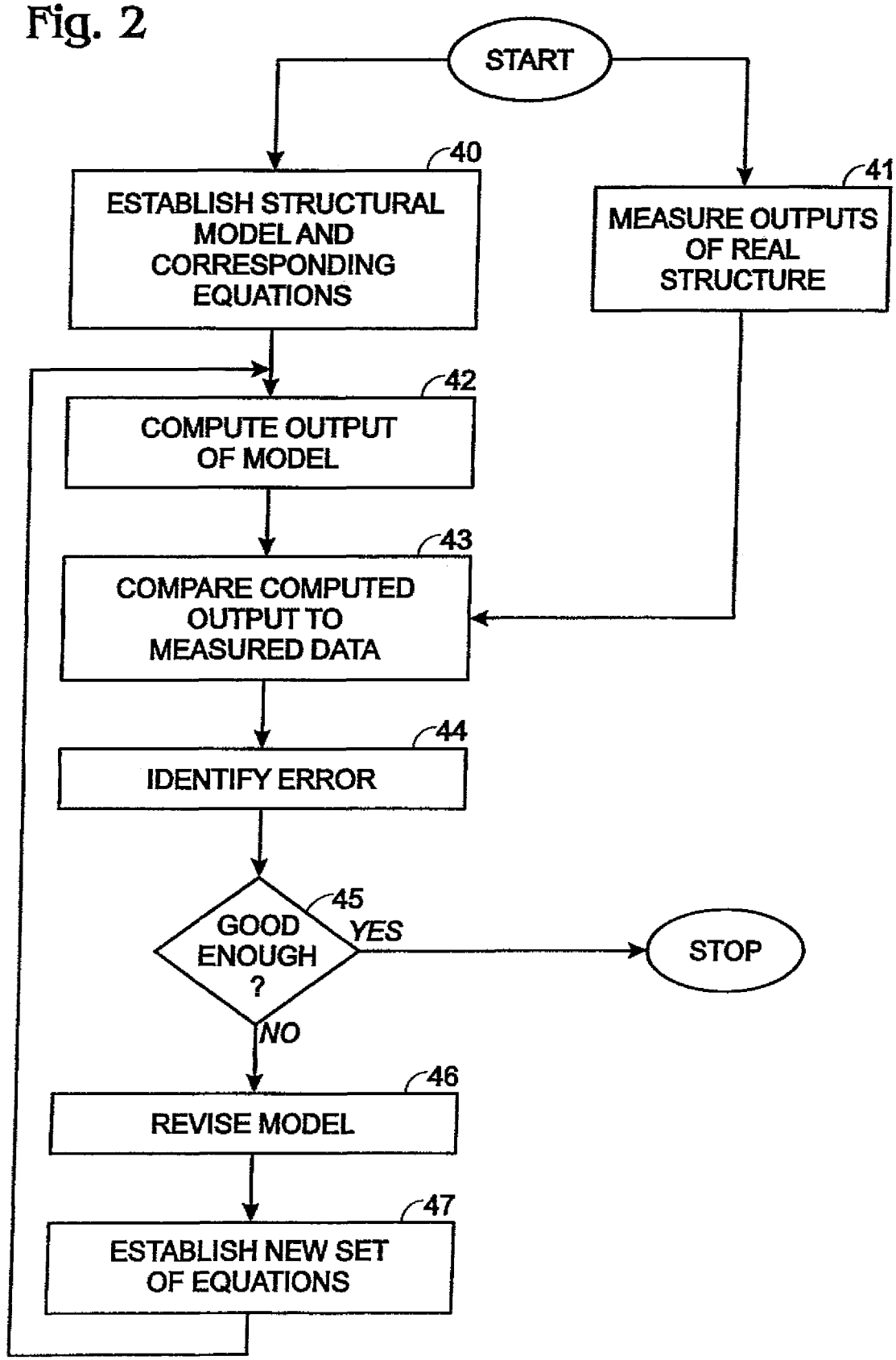
FIG. 2 is a flow diagram of a standard method for solving an inverse problem.

In a first embodiment of the invention, the invention utilizes EIT in conjunction with either EEG and MREIT. In the case of the former, the EIT is utilized as a dynamic neural function imaging tool, and in the case of the latter, it is utilized either as a static tissue impedance modeling tool or as a dynamic neural function imaging tool. Thus, the invention can best be understood by considering each of the following three aspects individually:

1) EIT (dynamic neural function imaging) in conjunction with EEG.
2) EIT (static tissue impedance modeling) in conjunction with MREIT
3) EIT (dynamic neural function imaging) in conjunction with MREIT.

It is recognized for purposes herein that impedance has both static and dynamic components. Static tissue impedance is that which characterizes tissues that are either not associated with a source, are if they are associated with a source, the source is not electrically Aactive@ in the sense of producing electrical currents (hereinafter Aneural currents@).

Neural function is the result of the activity of active sources, which cause changes in impedance in surrounding tissues. The corresponding dynamic impedance components have periods on the order of 10 ms or less. ADynamic neural function imaging@ refers to mapping the locations of tissues exhibiting dynamic impedance components.

In general, the invention is particularly adapted for use in probing tissues internal to the head, with the objective being to probe an electrically active brain; however, it is to be understood that methods described herein may be utilized for probing any other internal body tissue.

Aspect 1: EIT (Dynamic Neural Function Imaging)/EEG

According to the first aspect of the invention, EIT is used as an imaging modality in conjunction with EEG, and will be referred to as a Adynamic@ EIT.

FIG. 1 shows a standard system 10 for performing an EIT generally, which may be used in accordance with the present invention. The system includes a sensor array 12 that is applied to the head 14 of a subject. The array includes a number of electrodes 16 that are preferably held in a controlled relationship to one another by a Asensor net@ 18. A preferred sensor net is described in the inventor=s U.S. Pat. No. 5,291,888; however, the sensor array may make use of any desired method or structure for applying the electrodes 16 to the head 14.

The electrodes are placed on the scalp so as to make as good an electrical contact therewith as is practical. Typically and preferably the electrodes are treated with a gel having an impedance that matches the impedance of the scalp surface, so as to maximize the electrical coupling between the scalp and the electrodes.

The electrodes 16 are individually controlled to act as current sources for injecting predetermined currents into the head 14. More particularly, a current source 22 is coupled to each of the electrodes 16 through respective, separate channels 24 (only three representative channels 24 are shown, for simplicity).

A computer system 26 is used to instruct the current source 22 to output, for each of the electrodes 16, a current that the computer system determines. The computer system 26 may be an ordinary type, including a CPU 26a, a memory 26b, and input and output ports 26c and 26d, respectively. The current source is coupled to the computer through the computer system=s output port 26d.

Also coupled to each electrode 16 through respective separate channels 28 is a voltage (potential) measuring apparatus 30 (only three representative channels 28 are shown, for simplicity). The measuring apparatus 30 is also coupled to the computer system=s output port 26d, and is adapted to measure the potentials at the electrodes on command of the computer system 26.

The computer system 26 controls the current source 22 so that each electrode 16, in turn, will inject a commanded current into the head 14, and the computer system controls the voltage measuring apparatus 30 to measure the voltage at each of the remaining electrodes. In addition, the measuring apparatus is also coupled to the input port 26c of the computer system, so that the measuring apparatus can report the measured potentials back to the computer system.

Based on the known injected currents and the measured potentials, the computer system 26 is adapted to compute the internal impedances that are presumed to exist at various points on a single (planar) slice through the head, by solving the aforementioned inverse problem for the slice.

The descriptions hereinafter will not further distinguish between a single slice and a volume comprising multiple slices, it being understood that a volume can be built up of slices, and that, therefore, the same principles will apply.

The details involved in solving the inverse problem are complex; they are, however, well known in the art and need not be described for purposes of understanding the invention. But it should be noted generally that the inverse problem involves solving a series of different sets of equations that relate input to output, where each set of equations corresponds to a unique hypothetical model. Solving the inverse problem involves solving one set of equations, corresponding to one model (e.g., an initial model), comparing the result with the real-world measurements, noting the error, and adjusting (or re-adjusting) the model so as to establish a revised set of equations, and so on.

So, referring to FIG. 2, there is in general, for solving any inverse problem, a step 40 of establishing a set of equations corresponding to a hypothesized model of the structure that it is desired to discern. The model may be an active model, meaning that it includes active elements, such as sources, or it may be a passive model, meaning that it has only passive elements, such as impedances. The equations define the output of the model, which in the case of a passive model is responsive to an applied input, and in the case of an active model exists even if there is no applied input. In the next step 42, this output is computed using the model.

Having no particular timing relationship with steps 40 or 42, there is also a step 41 of measuring the corresponding output of the real structure. This step may be performed as many times as desired, but typically it is performed only once.

In step 43, the output of step 42 is compared to the measured data, and the (inevitable) error is identified in step 44. Then, in step 46 a revised hypothesized model is selected, and in step 47 a set of equations corresponding to the revised hypothesized model are established. After this, step 42 is repeated; and steps 42-47 are repeated until the error appears to be minimized, or is otherwise considered acceptable (step 45).

Using the system 10, potential measurements are made in response to injected currents in the physical manner described above. However, it is recognized that, as a result of source activity, there will be changes in the measured potentials, due to changing impedances, when there are no changes to the injected currents. So for imaging, potentials are measured over time while holding the injected currents constant.

The dynamic EIT inverse problem is to deduce the locations of the sources of changes in impedance that would be necessary to produce the pattern of potential changes measured at the electrodes 16. As noted above, the potential changes are small, rendering the inverse problem in the case of EIT imaging to be extremely ill posed.

To improve the performance of EIT as a dynamic neural function imaging method, the present invention provides for solving the dynamic EIT inverse problem by utilizing an EEG Aimage,@ i.e., a source localization, of the activity of the sources responsible for the dynamic impedance.

Thus, an EEG procedure is also performed using the same system 10. The current source 22 is not utilized; but the potential measuring apparatus 30 may be utilized now to essentially continuously monitor the electrical potentials at the sensors 16.

It is recognized as being important to use the same electrodes 16, as they are installed for performing the dynamic EIT, to perform the EEG. In that case, there is a Areciprocity,@ whereby the pathways taken by the injected currents, and therefore characterized by the EIT, will be the same paths taken by the neural currents characterized by the EEG. This is recognized to provide for enhanced Aconvergence@ of the solution to the dynamic EEG inverse problem.

Hereinafter, it will be understood that reference herein to the Asame electrodes@ does not necessarily mean that the electrodes are physically the same—what is intended is to ensure that they are in the same locations. This is most conveniently and preferably ensured by using the same electrodes, and it is necessary that the electrodes be physically the same as well as in the same locations when they are being used for two purposes simultaneously.

It is the case here that the EIT and EEG measurements are to be taken simultaneously, so that they are responsive to the same underlying neurophysiological activity, i.e., the dipolar fields produced the sources in the case of EEG and the associated ionic transfers between the neurons and the neighboring extracellular spaces in the case of dynamic EIT.

Based on the measured potentials, the computer system 26 is adapted to solve an EEG inverse problem for the locations of the sources, following the general methodology described above in connection with FIG. 2. The EEG source localization problem is well known and need be described no further, except that it requires specification of static internal tissue impedances, so a model of static tissue impedances is required. Preferably, such a model is obtained by use of another EIT, referred to herein as a Astatic@ EIT.

It is recognized as being important to use the same electrodes 16, as installed for performing the EEG, for performing the static EIT. In that case, there is a Areciprocity,@ whereby the pathways taken by the injected currents, and therefore characterized by the EIT, will be the same paths taken by the neural currents characterized by the EEG. This is recognized to provide for a an impedance model that is tailored for use in solving the particular EEG inverse problem, as disclosed in the inventor=s U.S. Pat. No. 6,594,521.

There is no particular required relationship between the times the static EIT and EEG procedures are conducted, since the static EIT is being used to measure static tissue impedance.

It may be noted that the static EIT inverse problem is to deduce the static impedance distribution that is necessary to transform the known injected currents into the potentials measured at the electrodes 16. The below-described second aspect is directed to improving this solution, and this improvement is preferably incorporated here.

It should also be noted that the EEG only Asees@ source activity that is coordinated with other source activity, i.e., a large number of neurons must Afire@ together to produce a measurable Afar field@ signal at the electrodes 16. Otherwise, if the sources fire randomly, the fields tend to cancel each other out in the aggregate. On the other hand, the EIT is not measuring the fields produced by the sources, and therefore it is not limited to Aseeing@ only impedance changes associated with neurons that are firing together. Rather, the EIT will respond to impedance changes whether as the result of coordinated neural activity or not. So it is possible that the EIT will be responsive to neural activity that the EEG cannot sense, and it might be expected that the EIT and EEG will not provide complementary, or convergent, measures.

However, it is recognized that the EIT and EEG will be responsive to the same neural activity if two conditions are met: (1) the activity occurs in a particular part of the brain, such as the cortex, in which the neurons are Aaligned,@ and (2) the neurons are firing synchronously. It is further recognized that these conditions can be met, based on the following considerations.

First, the inverse problem is based on an assumed head model, and the anatomical significance of the model locations of tissues undergoing impedance changes is specified by the model. For example, the head model will specify the volume of space assumed to be occupied by cortex. Any proposed solution to the inverse problem for specifying the locations of tissue undergoing impedance changes will specify locations for such tissues. Whether those locations are in the volume of space assumed to be occupied by cortex will be known. If they are, it can be assumed that the measured impedance changes associated with those tissues will be reflected in the EEG. Preferably, to improve the accuracy of such assumptions, the head model is based on measured data, such as Mill data, established for the particular head 14.

Second, while it remains that the neurons may not fire synchronously, during any given short time period, if the neurons are firing asynchronously, there will be fewer of them firing at any given time than if they all fired together at that time. Thus, over a short time interval, only a relatively small fraction of the neurons are firing. This is important because the EIT (like EEG) has very good temporal resolution, so it can discriminate between impedance changes occurring during short time intervals and changes that occur during other times. Thus, the EIT does not see a single impedance change resulting from the aggregate of asynchronous neural firings over longer times; instead, the EIT sees, instant-by-instant, a constant, relatively low level of impedance change corresponding to the relatively small fraction of neurons that fire within an instant.

In the context of the present invention, this is a useful characteristic, because the EIT (again like EEG) also has very poor signal to noise discrimination. Therefore, the EIT will not be sensitive to these instant-by-instant impedance changes, due to their relatively low magnitude.

So, it is recognized that the EIT is usefully non-responsive to asynchronous neural activity, and so is usefully correlated with the EEG, which is also not responsive to asynchronous neural activity, in areas of the brain in which the neurons are aligned, such as the cortex.

The injected currents are of sufficiently small magnitude that they do not provoke a brain response, typically about 10 milliamps. The injected currents are also provided at a specific frequency, typically 200 Hz, and thus simply filtering the EEG measurements to exclude signal at the frequencies of the injected currents is sufficient to ensure that the EEG measurements are not contaminated by simultaneous current injection.

Moreover, the injected currents are typically provided within a narrow frequency range, such as +/−1 Hz, so that very little EEG signal need be lost as a result of the filtering.

According to this second aspect of the invention, the EEG inverse problem described above in connection with the first aspect is solved, and the solution is used as a Bayesian constraint on the solution to the EIT inverse problem.

The Bayesian constraints are conditional probabilities, particularly considering here the likelihood that a given model of the locations of tissues undergoing impedance changes should be chosen in light of the source locations obtained by solving the EEG inverse problem. For example, one may consider whether to place a source at a given location in light of an indication obtained by solving the EEG inverse problem that the source closest to that location is probably some distance A away.

The EEG results are weighted, as probabilities, as desired to influence to a desired degree of confidence the solution to the EIT inverse problem. In the limit where the weighting factor for the EEG results is A1,@ (100%) the EEG results would completely govern, and there would be no advantage to combining with EIT. At the other extreme, if the weighting factor for the EEG results is A0,@ the EIT results would completely govern and there would be no advantage to combining with EEG. The EIT is a particularly weak imaging method, so it is desirable to weight the EEG results at greater than 50%; however, as noted above, the EEG does not see all the impedance changes that the EIT will see, and this is recognized to be a reason to discount the EEG results somewhat more than they otherwise would be. Balancing these considerations, the EEG results are preferably weighted in the range of 70-90%.

If the weighting factors are judiciously chosen, or if the actual conditional probabilities are determined, EIT combined with EEG will provide better spatial resolution than EEG alone.

The Bayesian constraints can be utilized at each iteration of steps 42-47, or they may be utilized less frequently, e.g., every other iteration, or only when there is a relatively high degree of uncertainty.

With reference to FIG. 3, the methodology of the second aspect of the invention is briefly reviewed as follows: In a step 100, an EIT procedure is performed, and in a contemporaneous step 102, an EEG procedure is performed on the head 14 using the same electrodes as used in the EIT procedure. In a step 104 either contemporaneous with or subsequent to step 100, a final solution to an EIT inverse problem defining a final model of the location of tissue in the head 14 that exhibited changes in impedance is obtained. In a step 106 subsequent to steps 100-104, the EEG inverse problem is solved, using the final solution to the EIT inverse problem from step 104 as a Bayesian constraint.

Aspect 2: EIT (Static Tissue Impedance Modeling)/ MREIT

According to the second aspect of the invention, static EIT is used for static tissue impedance modeling, and the impedance model so obtained is combined with another static impedance model obtained by use of MREIT.

The EIT static tissue impedance model is obtained as described above in connection with the source localization procedure of the first aspect of the invention. An MREIT impedance model is also obtained in the standard manner, except that the MREIT and EIT procedures according to the invention will utilize the same electrodes 16, as installed for performing the EIT, to perform the MREIT. In that case, there is a Areciprocity,@ whereby the pathways taken by the injected currents characterized by the EIT will be the same paths taken by the injected currents that are imaged in the MREIT. This is recognized to provide for enhanced Aconvergence@ of the solution to the EIT inverse problem.

There is no particular required relationship between the times the EIT and MREIT procedures are conducted, since both the EIT and MREIT are being used to measure static impedance.

The static EIT inverse problem is to deduce the static impedance distribution that is necessary to transform the known injected currents into the potentials measured at the electrodes 16. To improve the performance of the EIT as a static tissue impedance modeling method, the present invention provides for solving this EIT inverse problem by utilizing the information available from the MREIT, as Bayesian constraints.

Essentially, the Bayesian constraints here are to consider the likelihood that a given model of the distribution of static impedance should be chosen in light of the distribution indicated by the MREIT. For example, one may consider whether to assign a static impedance value of X to a given location in light of an indication from the MREIT that the impedance value at that location is probably Y.

The MREIT results are weighted, as probabilities, as desired to influence to a desired degree of confidence the solution to the EIT inverse problem. In the limit where the weighting factor for the MREIT results is A1,@ the MREIT results would completely govern, and there would be no advantage to combining with EIT. At the other extreme, if the weighting factor for the MREIT results is A0,@ the EIT results would completely govern and there would be no advantage to combining with MREIT. Since EIT and MREIT are comparably reliable modalities for static tissue impedance modeling, the MREIT results should generally be weighted at about 50% (e.g., in the range 45-55%); however, the balance can be struck as desired or as needed depending on the particular case.

If the weighting factors are judiciously chosen, or if the actual conditional probabilities are determined, combining EIT and MREIT will provide better spatial resolution for the impedances than either EIT or MREIT alone.

With reference to FIG. 4, the methodology of the third aspect of the invention is reviewed as follows: In a step 200, an EIT procedure is performed, and in another step 202 which bears no particular timing relationship to step 200, an MREIT procedure is performed using the same electrodes as used in the EIT procedure, to the point of obtaining a magnetic resonance image. In a step 204 subsequent to step 202, an EIT inverse problem defining a static tissue impedance model for the head 14 is solved, using the magnetic resonance image from step 202 as a Bayesian constraint.

Aspect 3: EIT (Dynamic Neural Function Imaging)/ MREIT

According to the third aspect of the invention, EIT is used for dynamic neural function imaging, as in the first aspect of the invention. However, in this case, the EIT inverse problem is constrained by MREIT, which is obtained in the manner described immediately above in connection with the second aspect of the invention. In particular, it is recognized as being important to use the same electrodes 16, as they are installed for performing the EIT, to perform the MREIT. In that case, there is a Areciprocity,@ whereby the pathways taken by the injected currents, and therefore characterized by the EIT, will be the same paths taken by the neural currents characterized by the EEG. This is recognized to provide for enhanced convergence of the solution to the dynamic EIT inverse problem.

In this case, the EIT inverse problem is to deduce the locations of the sources of changes in impedance that would be necessary to produce the pattern of potential changes measured at the electrodes 16. To improve the performance of the EIT as a dynamic neural function imaging method, the present invention provides for solving this EIT inverse problem by utilizing the information available from the MREIT, particularly as Bayesian constraints.

Essentially, the Bayesian constraints here are to consider the likelihood that a given model of the locations of impedance changes should be chosen in light of the impedance distribution indicated by the MREIT.

It is particularly important in this context to note that the MREIT is substantially slower than EIT. Typically, the MREIT averages (or integrates) over a time period of about 200 ms, and Afast@ MREIT may lower this period to 50 ms; whereas the changes in impedance to be discerned are occurring within periods of 10 ms or less. On the other hand, the MREIT has significantly better spatial resolution than EIT.

The present inventor has recognized that these two modalities are particularly complementary, i.e., the MREIT has very good spatial resolution but very poor temporal resolution; whereas the EIT has very poor spatial resolution, but very good temporal resolution. The inventor has also recognized that MREIT, though slow, is not so slow that it fails completely to Asee@ the impedance changes that are seen by the EIT, i.e., both imaging modalities are recognized as being able to Asee@ the impedance changes. Accordingly, utilizing the MREIT as a Bayesian constraint on the solutions to the EIT inverse problem will result in an image of dynamic neural function that has better temporal resolution than that of the MREIT, and better spatial resolution than that of the EIT.

The weighting factors may be chosen to reflect the extent to which improved spatial resolution is preferred over improved temporal resolution, and vice versa. At a 50% weighting, both of these characteristics will be about equally improved.

The EIT potential measurements are made simultaneously with the MREIT, i.e., simultaneous with the magnetic resonance imaging and the current injection occurring during the time required to acquire the magnetic resonance image. This is accomplished by using the same current injection step for both the EIT and MREIT, i.e., the same currents applied at the same times at the same locations on the head surface are used in both EIT procedures.

With reference to FIG. 6, the methodology of the fourth aspect of the invention is briefly reviewed as follows: In a step 300, an EIT procedure is performed, and in a contemporaneous step 302, an MREIT procedure is performed on the head 14 using the same electrodes as used in the EIT procedure, to the point of obtaining an MREIT impedance model. In a step 304 either contemporaneous with or subsequent to step 300, an EIT inverse problem defining the location of tissue in the head 14 that exhibited changes in impedance is solved, using the MREIT impedance model from step 302 as a Bayesian constraint.

Second Embodiment

In a second embodiment of the invention, the first embodiment is utilized in conjunction with neurostimulation, which for purposes herein is stimulation of neural activity in the brain by the injection of stimulating currents into the head. The same system described above for performing EIT according to the first embodiment can be utilized for neurostimulation. However, whereas the injected currents utilized in the first embodiment can be on the order of $10^{-4}$ amps (100 microamps), and are small enough not to provoke a discernible brain response, the injected currents utilized in neurostimulation are two orders of magnitude larger (about 10 milliamps) so that they will provoke a brain response, which may persist for several seconds after their cessation.

The usual objective of neurostimulation is to stimulate the aforementioned Asources@ of neural activity in a subject=s brain, typically for the purpose of causing the sources to become active as they would as a result of the subject=s will, i.e., without the stimulation. In such cases, the EEG potentials associated with the active sources will be known, and the sources will have been localized, preferably according to the first aspect of the first embodiment, in which an EIT static impedance model of the head tissues is utilized in the solution to the EEG inverse problem, utilizing the same electrodes for both the EIT and EEG.

The EEG thus provides a model of where the sources are located, and the static EIT provides a model from which the impedance from each electrode to each of the sources can be determined. From these models, the current that will flow to each of the sources as a result of a given voltage applied to a given electrode can be computed in a standard manner, and the current flows resulting from voltages applied to all the other electrodes can be superimposed.

So far, injected stimulative currents have been applied according to a predetermined plan, to provide a level of stimulation that is intended to result in causing the sources to become active to substantially the same extent that they were previously active on their own. However, the plan will be subject to errors, so it is an outstanding feature of the invention to monitor the stimulation to see whether the effects are those that are desired. For example, monitoring may show whether and how effectively the currents are flowing to the locations that it is desired to stimulate, and monitoring may also show whether and to what extent expected patterns of response for the type of activity that it is desired to stimulate are actually occurring.

To monitor the currents, the currents could be imaged with MRI, and to monitor the effects, EEG potential measurements could be used. However, the present inventor has recognized that these monitors are insufficient. Specifically, the MRI is insufficient because of its poor temporal resolution, and the EEG is insufficient because of its poor signal resolution. According to the present invention, these insufficiencies are overcome by utilizing the first embodiment of the invention as a monitor; particularly, any one or more of the aforedescribed three aspects thereof.

So, according to the second embodiment of the invention, the first embodiment of the invention is utilized to monitor the results of neurostimulation, and the information provided by this monitoring is utilized as feedback for adjusting the originating location (e.g., which of the electrodes 16 is used), magnitude, and/or timing of the stimulating currents, so that the stimulation is more effective to produce the result sought.

It will be noted that EIT is utilized in all three aspects of the first embodiment of the invention, and that EIT utilizes a relatively low level current injection. So it will be appreciated that the second embodiment of the invention utilizes two current injections, a relatively high level current injection for stimulation and a relatively low level current injection for impedance measurement. It is recognized by the present inventor that these two current injections can be either sequential or simultaneous.

Current injections are generally performed by selecting certain electrodes 16 and applying to those electrodes a positive potential relative to other selected electrodes 16, the former therefore being sources of the injected current (hereinafter referred to as Ainjection sources@ to distinguish over the Asources@ of neural activity), and the latter being sinks for the injected current (hereinafter Ainjection sinks@). The step of applying the potentials to a pair of electrodes will be referred to herein as Aactivating@ the electrodes of the pair.

Typically, though not necessarily, the EIT current injections (and so too the MREIT current injections when EIT is combined with MREIT) are performed by a Ascanning@ method of sequentially selecting and activating various single pairs of the electrodes 16 to function as injection sources and injection sinks. On the other hand, the neurostimulative current injections are preferably and typically performed by selecting in advance particular injection source/injection sink pairs and activating the pairs simultaneously.

To reiterate, the relatively high level stimulative currents that are employed for the purpose of stimulating source activity in the brain may be injected either sequentially or simultaneously with the EIT (or MREIT) relatively low level current injections that are employed for the purpose of monitoring the stimulated activity (hereinafter Amonitoring currents@).

Where the stimulative and monitoring currents are applied at different times, the stimulative currents are applied first, and the monitoring currents may be applied at any subsequent time at which the sources remain, at least to a discernible extent, stimulated. It is has been found that this can be up to several seconds after the stimulus has been removed.

Where the stimulative and monitoring currents are applied at the same time, there is no need to subtract the effects of the former from measurements responsive to the latter. As noted above in connection with the first embodiment, the EIT (or MREIT) injected currents are provided within a narrow frequency range. Moreover, this frequency range is or can be made to be relatively high as compared to the frequency of the brain activity that is being stimulated. On the other hand, the stimulative currents must be resonant with the frequency of the stimulated source activity. So the EIT (or MREIT) currents are or can be made to be independent of the stimulative currents, and therefore the two sets of currents linearly superimpose. Therefore, if the monitor is to employ either the second or third aspects of the first embodiment, no special steps will be required to avoid contamination resulting from the stimulation.

Also, because of the linear independence of the monitoring and stimulating currents, it is recognized that the same electrodes can be used simultaneously to inject both types of currents. This is also recognized as being preferable.

The EEG, however, measures signal at the frequency of the stimulating currents, so the EEG may be heavily contaminated by the stimulation if appropriate ameliorative steps are not taken. As is readily apparent, the EEG and EIT measures can be performed in sequence, after the stimulation has ceased to avoid contamination. However, preferably, the monitor is made available during the stimulation. The present invention solves the contamination problem in this circumstance by using the computer system 26 to compute the effect, at the location of each of the monitoring electrodes 16, of the stimulating currents, using a static EIT tissue impedance model, and subtracting or otherwise mathematically accounting for this effect from the measured potentials at the same electrodes.

The static EIT is performed as described above in connection with the first embodiment. It is reiterated that there need be no particular timing relationship between the static EIT for this purpose, and either the stimulation or the EEG.

In the second embodiment where EIT and neurostimulation are performed simultaneously, the invention can also be used for synchronizing the source activity to the neurostimulative currents, and thereby shifting the time of first occurrence of the source activity, which will be referred to herein as shifting its Aphase.@ The objective in this case is not to stimulate activity that would not otherwise occur, but to shift the phase of activity that is already occurring or will otherwise occur.

Synchronization is the result of the stimulative currents changing the polarization of the neural membranes, and thereby changing their sensitivity to synaptic inputs. It is a known problem that it is difficult to Afocus@ the stimulative currents on the particular neurons of interest. However, in the case of neural activity that is already occurring, or that is about to occur without stimulation, the neurons are at or near the Athreshold@ for firing. In that case, it is recognized by the present inventor that neurostimulative currents will preferentially impact those particular neurons, and their effects on other areas of the brain can be ignored.

As a rule, Aneurons that fire together wire together,@ meaning that when neurons fire in concert, their synaptic connectivities tend to be recorded, or learned, by the brain, whereas if the neurons are out of phase with one another, this learning will either not occur at all, or if it does occur, it occurs less effectively. The present inventor has recognized that synchronizing neural activity according to the invention is therefore useful for either learning or unlearning particular patterns of neural activity. Thus, it may be desirable to modify the timing of the stimulating currents either to bring neural activity into better synchronization or not. To achieve either result, it is important to be able to Asee@ the source activity in real time, with millisecond-by-millisecond resolution, to monitor the effect of the neurostimulative currents on the phase of the activity, and the invention provides this critical capability.

It is not considered important to the quality of the result to utilize the same electrodes for the neurostimulation and the EIT; however, this may be a practical advantage in some cases.

It is to be understood that, while specific uses of EIT have been shown and described as preferred, other configurations and methods could be utilized, in addition to those already mentioned, without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A method for controlling neural activity in a brain, comprising:
   performing a source localization procedure for localizing one or more sources of the neural activity including measuring electrical potentials produced by one or more sources of the neural activity and obtaining one or more solutions to an inverse problem for localizing said one or more sources posed by said electrical potentials;
   performing a neurostimulation procedure in addition to the source localization procedure by application of one or more stimulating currents into the brain to stimulate said one or more sources and provoke a response; and
   using said source localization procedure as a monitor to provide for feedback control of said neurostimulation procedure, wherein said monitor provides for monitoring one or more effects on the brain of said one or more stimulating currents utilizing said one or more solutions, and wherein said feedback control includes modifying at least one of an originating location, magnitude, and timing of at least one of said one or more stimulating currents in response to said monitoring.

2. The method of claim 1, wherein said feedback control provides for synchronizing the neural activity to said one or more stimulating currents.

3. The method of claim 2 for synchronizing the neural activity to said one or more stimulating currents, wherein said monitoring includes observing a phase of electrical activity produced by at least one of said one or more sources, and wherein said feedback control includes modifying said timing so as to shift said phase.

4. A system for controlling neural activity in a brain, comprising:
   a plurality of electrodes and corresponding potential measuring devices configured for measuring electrical potentials produced by one or more sources of the neural activity;
   a plurality of electrodes and corresponding current sources configured for injecting one or more stimulating currents into the brain that either alone or in combination are sufficiently large magnitude to provoke a substantial brain response, for stimulating said one or more sources; and
   one or more computers configured for obtaining one or more solutions to an inverse problem for localizing said sources posed by said electrical potentials, monitoring one or more effects on the brain of said one or more stimulating currents utilizing said one or more solutions, and providing for feedback control of the neural activity, said feedback control being applied to said current sources to modify at least one of an originating location, magnitude, and timing of at least one of said one or more stimulating currents in response to said monitoring.

5. The system of claim 4, for synchronizing the neural activity to said one or more stimulating currents, wherein said monitoring includes observing a phase of electrical activity produced by at least one of said one or more sources, and wherein said feedback control includes modifying said timing so as to shift said phase.

\* \* \* \* \*